United States Patent
Siewerdsen et al.

(10) Patent No.: US 9,427,286 B2
(45) Date of Patent: Aug. 30, 2016

(54) METHOD OF IMAGE REGISTRATION IN A MULTI-SOURCE/SINGLE DETECTOR RADIOGRAPHIC IMAGING SYSTEM, AND IMAGE ACQUISITION APPARATUS

(71) Applicant: SIEMENS AKTIENGESELLSCHAFT, Munich (DE)

(72) Inventors: Jeffrey Siewerdsen, Baltimore, MD (US); Yoshito Otake, Baltimore, MD (US); Ali Uneri, Baltimore, MD (US); J. Webster Stayman, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 55 days.

(21) Appl. No.: 14/034,845

(22) Filed: Sep. 24, 2013

(65) Prior Publication Data

US 2015/0085981 A1 Mar. 26, 2015

(51) Int. Cl.
*A61B 6/00* (2006.01)
*A61B 19/00* (2006.01)

(52) U.S. Cl.
CPC .......... *A61B 19/00* (2013.01); *A61B 2090/367* (2016.02); *A61B 2090/3764* (2016.02)

(58) Field of Classification Search
USPC .............................................. 378/98.8, 98.12
See application file for complete search history.

(56) References Cited

U.S. PATENT DOCUMENTS

| 7,620,144 B2* | 11/2009 | Bodduluri ................ A61B 6/02 378/41 |
| 7,949,089 B2* | 5/2011 | Dafni .................... A61B 6/022 378/6 |
| 8,280,491 B2 | 10/2012 | Kuduvalli et al. |
| 9,039,282 B2* | 5/2015 | Maschke .............. A61B 6/4411 378/197 |
| 2012/0063564 A1* | 3/2012 | Klingenbeck ..................... 378/4 |
| 2014/0049629 A1 | 2/2014 | Siewerdsen et al. |
| 2014/0247919 A1* | 9/2014 | Zhang .................... A61B 6/025 378/62 |
| 2015/0043712 A1* | 2/2015 | Wang .................... A61B 6/022 378/42 |

FOREIGN PATENT DOCUMENTS

| WO | 2005024721 A2 | 3/2005 |
| WO | 2012149548 A2 | 11/2012 |

OTHER PUBLICATIONS

Siddon, Robert L., "Fast calculation of the exact radiological path for a three-dimensional CT array" Department of Radiation Therapy and Joint Center for Radiation Therapy, Harvard Medical School, Boston Med. Phys. 12 (2), Mar./Apr. 1985, pp. 252-255.

(Continued)

*Primary Examiner* — Phillip A Johnston
(74) *Attorney, Agent, or Firm* — Laurence A. Greenberg; Werner H. Stemer; Ralph E. Locher

(57) ABSTRACT

A method, an imaging apparatus and a computer readable medium are enabled for automatically registering medical images. The imaging apparatus may be an amended C-arm. The image acquisition apparatus has a primary x-ray source and at least one auxiliary x-ray source, a detector for receiving radiation of the primary and auxiliary x-ray source, and an interface to a registration unit. The registration unit computes a 3D/2D registration of a provided 3D image and at least two acquired 2D images. An output interface is configured to provide an output and to display the registered images on a monitor.

15 Claims, 6 Drawing Sheets

(56) References Cited

OTHER PUBLICATIONS

Otake, K et al, "Automatic localization of vertebral levels in x-ray fluoroscopy using 3D-2D registration: a tool to reduce wrong-site surgery", Physics in Medicine and Biology vol. 57, Issue 17 (2012), pp. 5485-5508.

Navab, N. et al, "3D Reconstruction from Projection Matrices in a C-Arm Based 3D-Angiography System", Siemens Corporate Research, Inc., Princeton, NJ, 1998, pp. 119-129.

Galigekere, R et al., "Cone-Beam Reprojection Using Projection-Matrices", IEEE Transactions on Medical Imaging, vol. 22, No. 10, Oct. 2003, pp. 1202-1214.

Otake, Y eta l., "Intraoperative Image-based Multiview 2D/3D Registration for Image-Guided Orthopaedic Surgery: Incorporation of Fiducial-Based C-Arm Tracking and GPU-Acceleration", IEEE Transactions on Medical Imaging, vol. 31, No. 4, Apr. 2012, pp. 948-962.

Hansen, N et al, "Evaluating the CMA Evolution Strategy on Multimodal Test Functions", Parallel Problem Solving from Nature, PPSN 2004; Springer-Verlag 2004.

Long, Y et al., "3D Forward and Back-Projection for X-Ray CT Using Separable Footprints", IEEE Transactions on Medical Imaging, vol. 29, No. 11, Nov. 2010, pp. 1839-1850.

Rogelj, P et al., "Point similarity measures for non-rigid registration of multi-modal data", Computer Vision and Image Understanding 92 (2003), pp. 112-140.

Otake, Y et al., "Robust 3D-2D Image Registration: Application to Spine Interventions and Vertebral Labeling in the Presence of Anatomical Deformation", John Hopkins University Baltimore MD, pp. 1-21.

Pluim, J. et al., "Image registration by maximization of combined mutual information and gradient information" IEEE Transactions on Medical Imaging, vol. 19, No. 8, Aug. 2000, pp. 1-6.

McLaughlin, R. A et al., "A Comparison of a Similarity-Based and a Feature-Based 2-D-3-D Registration Method for Neurointerventional Use", IEEE Transactions on Medical Imaging, vol. 24, No. 8, Aug. 2005 pp. 1058-1066.

Otake, Y et al, "Automatic localization of vertebral levels in C-arm fluoroscopy: evaluation of the LevelCheck algorithm in a preclinical cadaver study with realistic tissue deformation"CARS 2013, Computer Assisted Radiology and Surgery; 27th International Congress and Exhibition (Heidelberg, Germany) (Jun. 2013), pp. 1-4.

Otake, Y et al., "Verification of surgical product and detection of retained foreign bodies using 3D-2D registration in intraoperative mobile radiographs", CARS 2013, Computer Assisted Radiology and Surgery 27th International Congress and Exhibition (Heidelberg, Germany) (Jun. 2013), pp. 1-4.

* cited by examiner

METHOD OF IMAGE REGISTRATION IN A MULTI-SOURCE/SINGLE DETECTOR RADIOGRAPHIC IMAGING SYSTEM, AND IMAGE ACQUISITION APPARATUS

BACKGROUND OF THE INVENTION

Field of the Invention

The present application lies in the field of image processing and computer technology and, in particular, pertains to image registration of volumetric medical images to two-dimensional radiography or fluoroscopy projection images.

A surgical guidance system is intended to assist a surgeon in localizing anatomical targets with respect to surgical instruments while helping to avoid injury to adjacent normal tissue. The predominant basis for surgical guidance involves dedicated tracking systems (e.g., optical or electromagnetic, EM) that track the location of predefined markers attached to the patient and surgical instruments. Navigation in the context of preoperative and/or intraoperative images (and surgical planning data therein) is achieved through registration of the coordinate system associated with the tracker with that of the image, most often using manual procedures such as touching predefined fiducials with a pointer (see, inter alia, Vahala E, Ylihautala M, Tuominen J, Schiffbauer H, Katisko J, Yrjänä S, Vaara T, Ehnholm G and Koivukangas J 2001 Registration in Interventional Procedures with Optical Navigator. Journal of Magnetic Resonance Imaging: JMRI 13 93-8).

2D imaging modalities such as x-ray projection (fluoroscopy) and video endoscopy are fairly common in the operating room—especially in minimally invasive procedures—but the information provided by such systems is most often only qualitatively interpreted, and there is growing interest in extending capabilities to accurately align the 2D data with respect to 3D images and planning. Compared to surgical trackers that follow a sparse set of features (i.e., fiducial markers), such images provide rich, up-to-date information that includes accurate depiction of anatomical deformation and resection within the region of interest. However, in the context of surgical guidance, they provide a limited (2D) view of the 3D scene and thereby seem limited in their utility for 3D localization—hence, the use of systems capturing multiple views (e.g., biplane imaging) for interpreting 2D images within a more accurate 3D context. For a human observer, biplane imaging (i.e., projections acquired with angular separation, $\Delta\theta \sim 90°$ is common, since it presents familiar (e.g., AP and LAT) anatomical views and simplifies the mental correspondence of two projection views with the 3D image and planning context.

Incorporation of preoperative 3D image and planning information into intraoperative 2D images via 3D-2D registration has been extensively investigated, showing utility in increasing the precision and accuracy of interventional radiology, surgery, and radiation therapy. Previous work in spine surgery (e.g., the "LevelCheck" method, (Otake et al 2012)) computes a 3D-2D registration to overlay the locations of target vertebrae as defined in preoperative CT onto intraoperative fluoroscopy. Such registration and visualization was specifically designed to assist the surgeon in localizing target anatomy (i.e., a specific vertebral level) and offers numerous potential advantages (e.g., reduced time, radiation dose, and error rates) in comparison to conventional methods such as manual level counting. The basic aim of such solutions is to project information from the 3D image accurately onto the 2D intraoperative image, thereby providing registration within a familiar image context that reliably depicts anatomy and the position of interventional devices during intervention (Weese et al 1997).

According to state of the art so called "bi-plane" fluoroscopy systems are known. FIG. 1 shows such a state of the art system in order to provide the interventionalist with 3D reckoning within the context of 2D x-ray projection data. As may be seen in FIG. 1, such systems typically involve two x-ray sources and detectors on separately controlled C-arms. Usually the two detectors are mounted on separate but integrated C-arms. Typical use involves projection images acquired at around 90° angular separation and "mental" registration/triangulation of the position of structures visible in the two projections. Some systems are beginning to offer computational 3D-2D registration on such systems as well (e.g., available on Siemens Artis bi-plane).

3D-2D registration offers means to compute the spatial relationship between a 3D volumetric image (e.g., CT image) and a 2D projection image (e.g., fluoroscopy). The registration allows reckoning of structures defined in the context of the 3D image (e.g., anatomy and planning data defined in preoperative CT) in a spatially accurate manner directly in the context of the 2D image (e.g., overlay of the position of such defined structures). 3D-2D registration can be computed from a single 2D projection view, which is known in state of the art (Otake et al.). Doing so allows, for example, accurate overlay of structures defined in CT directly on a projection image—as in the overlay of vertebrae labels with the "LevelCheck" algorithm of Otake et al. However, although 3D-2D registration from a single projection image is sufficient to align such structures in the 2D domain of the projection, registration from a single projection does not give accurate 3D localization of such structures due to a lack of depth resolution, which is the pertinent information in precise image-guided interventions—e.g., guiding an interventionalist to place a device (e.g., a needle) on a target (e.g., a tumor). Registration from a single projection would be subject to large errors in "depth" localization (i.e., along the direction of the axis connecting the x-ray source and detector) and would not likely be sufficient to guide the interventionalist accurately in the 3D domain of the patient.

Therefore, in state of the art it is known to use two or more 2D projections for image registration. 3D-2D registration from two (or more) projections provides the capacity for accurate 3D localization. This is analogous to the "mental" registration performed by the interventionalist using bi-plane fluoroscopy, as mentioned above, but can operate algorithmically, with a fairly high degree of accuracy in the registration (e.g., <2 mm error in the 3D domain), and can operate on projections acquired at less than 90° angular separation between the two projections.

Possible means for acquiring two (or more) projections suitable to 3D-2D registration (and accurate 3D localization) include: At first, bi-plane systems or, secondly, motion of a single-plane system across some extent of angular separation to provide disparate projection view angles. The first has the disadvantage of requiring bulky complex systems (with two separate C-arms). The second has the disadvantage of slower speed and mechanical motion required in moving the single-plane system between two (or more) angles.

There is therefore a need to provide an improved image acquisition device which allows for an efficient and precise and accurate image registration procedure without the need to use markers.

BRIEF SUMMARY OF THE INVENTION

It is accordingly an object of the invention to provide a method and a system for automatically registering medical images which overcome various disadvantages of the heretofore-known devices and methods of this general type and which provides for an improved registration for medical imaging.

With the foregoing and other objects in view there is provided, in accordance with an aspect of the invention, a method that comprises the steps of:

providing a 3D image (for example with a computed tomography scanner (CT));

physically measuring or acquiring at least two 2D images on an acquisition device having a primary source and at least one auxiliary source and one common detector for the primary and the auxiliary source;

computing a 3D/2D registration of the provided 3D and the acquired 2D images; and outputting a result of the computed registration.

Computing the 3D/2D registration of the provided 3D and the acquired 2D images is preferably executed without using markers or a marker-based system. However, it has to be mentioned that the present invention is compatible with a system that does use markers. But registration does not require a marker system.

It has to be noted that the 3D image needs not necessarily be acquired with the same acquisition device as the at least two (projection) images. In a first embodiment the 3D image is acquired by a CT-Scanner and the at least two 2D images are acquired by an image acquisition device with the specific configuration according to the present invention with the multiple source and single detector system. In another embodiment the 3D image and the at least two 2D images are acquired by the same acquisition device with the specific configuration according to the present invention with the multiple source and single detector system.

According to another aspect of the present application the 2D images are acquired in parallel to the acquisition of the 3D image.

Computing the 3D/2D registration comprises:

iteratively computing a 2D projection view from the provided 3D image; and computing a target 2D projection view which best matches the acquired 2D image by using a numerical optimization that maximizes similarity between the two images.

It has to be noted that an update frequency for computing the 3D/2D registration may differ from the update frequency of acquiring the at least two 2D images.

According to another aspect there is provided an image acquisition apparatus, for example a modified C-arm, for medical imaging, wherein the (conventional) C-arm is adapted in construction in order to comprise:

a primary x-ray source;

at least one auxiliary x-ray source;

a detector for receiving radiation of the primary and auxiliary x-ray source;

an interface to a registration unit, which is adapted to compute a 3D/2D registration of a provided 3D image and at least two acquired 2D images according to the method described above;

an output interface which is adapted to provide an output and to display the registered images on a monitor.

According to an aspect the image acquisition apparatus, particularly the C-arm is adapted to provide the 3D image and the at least two 2D images.

According to a further aspect of present invention the 3D image is acquired by a (separate or additional) CT-scanner.

According to another aspect of present invention the primary and the at least one auxiliary x-ray source are mounted on a common support structure. The common support structure may be a ceiling mounted support member. Alternatively, the common support structure may be mounted on a moveable arm. In another embodiment the common support structure is positioned beneath an operating table and the detector is mounted above the operating table.

The method mentioned above or the registration may be implemented in software. Thus, present invention also refers to a non-transitory computer readable medium containing computer-readable instructions stored therein for causing a computer or a computer processor to perform the steps of the method mentioned above. The invention also might be implemented in hardware or in hardware modules combined with software modules. The hardware modules are then adapted to perform the functionality of the steps of the method, described above. Accordingly, it is also possible to have a combination of hardware and software modules. The modules are preferably integrated into an existing medical environment, for example into an acquisition device.

Other features which are considered as characteristic for the invention are set forth in the appended claims.

Although the invention is illustrated and described herein as embodied in an image registration in a multi-source/single detector radiographic imaging system, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings. The figures illustrate principles of the invention according to specific embodiments. It will be understood that it is also possible to implement the invention in other embodiments. The figures should be construed as examples only. Moreover, in the figures, like reference numerals designate corresponding modules or items throughout the different drawings.

DESCRIPTION OF THE INVENTION

In the following a short explication and definition of terms used in this disclosure is given.

The 3D volumetric image (i.e. CT image) is usually taken in a preoperative phase. Alternatively, the 3D image may also be acquired intraoperatively. The 3D image may also be provided from a memory buffer over an interface. For the purpose of registration 2D projection (views) are computed from this 3D image (for example as a digitally reconstructed radiograph, abbreviated as DDR).

The 2D images are physically acquired with the acquisition device according to the present invention with a multiple source and single detector configuration. The 2D images are also named fluoroshots or fluoroscopy images and are acquired during medical surgery. The 2D images may be provided via C-arm fluoroscopy. X-ray fluoroscopy provides 2D images showing patient anatomy and interventional devices within the patient, allowing qualitative interpretation by the interventionalist. For purposes herein, "fluoroscopy" is simply the acquisition of a series of x-ray projection images (showing, for example, motion or real-time guidance), and "radiography" refers to the acquisition of a single x-ray projection (radiograph). Projection images provide visualization of anatomy and devices in the 2D domain of the projection image but do not give 3D localization with respect to the 3D domain of the patient.

The terms "primary" and "auxiliary" source are to be construed as x-ray sources which are integrated in one common structure (i.e. C-arm).

Computing the 3D/2D registration refers to an automatic procedure which may be implemented in software and/or in hardware. Computing, thus, involves activating or "firing" the auxiliary source. For example, the "normal" 2D fluoroscopy image acquisition could proceed at a fairly high rate (often as high as 30 frames per second or even faster), whereas the registration (firing the auxiliary source) can be done at a much lower interval (every 1 seconds or every 10 seconds or on command from the surgeon) to provide updates to registration at a lower rate consistent with the needs of the surgeon in 3D localization.

The "outputting" refers to providing a registration result. The registration result may be displayed on a monitor and/or may be forwarded to other computer-based instances or may be further processed. The output may be a common graphical representation of registered 3D and 2D images. The common representation may comprise image or image part overlays. The images may be processed according to the DICOM standard (DICOM: Digital Imaging and Communications in Medicine).

Figure 1:
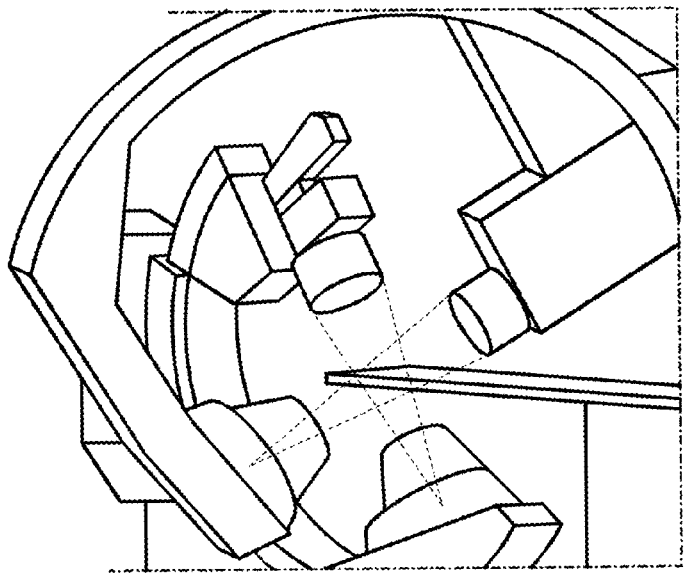
FIG. 1 is an exemplary representation of a bi-plane fluoroscopy system according to a state of the art system.
Figure 2:
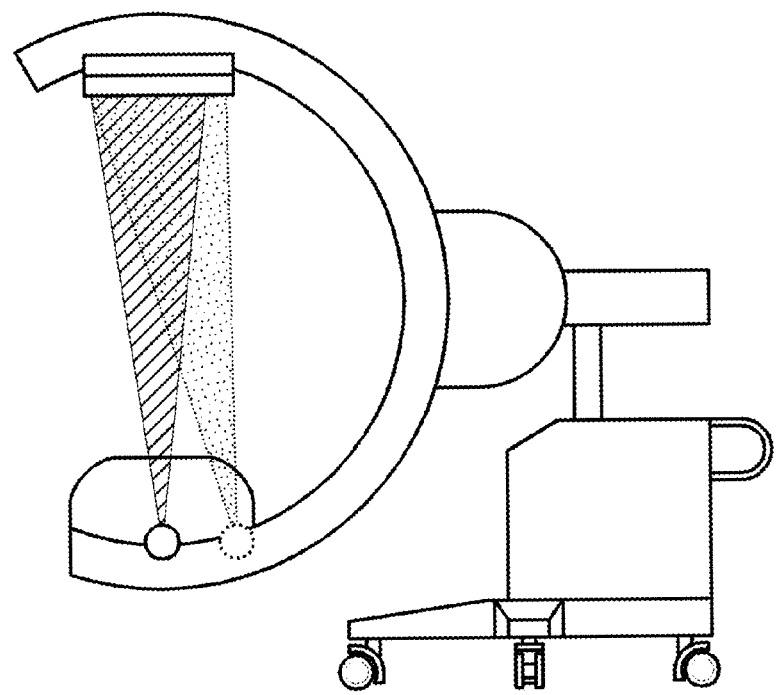
FIG. 2 is an exemplary representation of an x-ray system according to a preferred embodiment of present invention.
Figure 3:
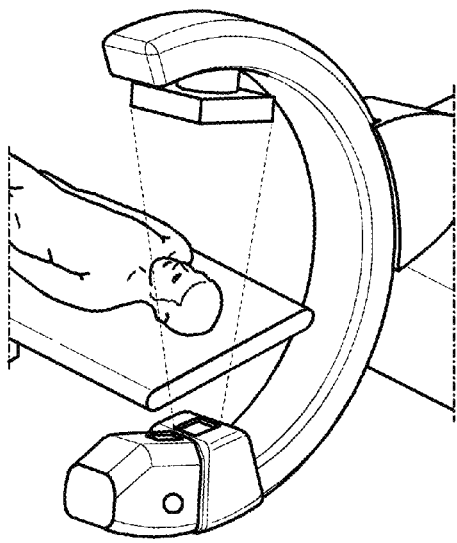
FIG. 3 shows an x-ray system, similar to the one depicted in FIG. 2 with an amended position of an auxiliary source
Figure 4:
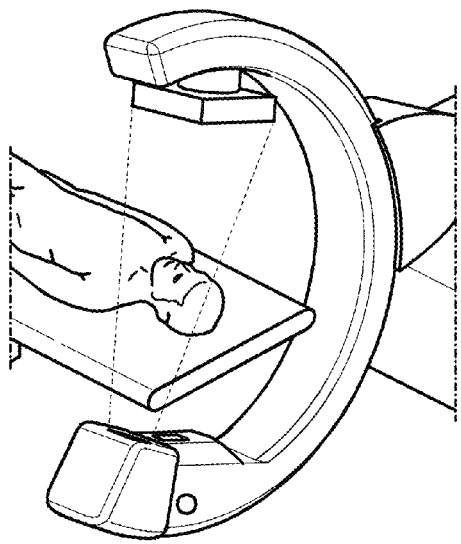
FIG. 4 to FIG. 6 show variations on the position of the auxiliary source in the exemplary embodiment depicted in FIG. 2.

A simple exemplary embodiment of the invention is illustrated in FIG. 2, involving two (or more) x-ray sources implemented on a single C-arm platform with a single x-ray detector. Recent work shows that even a fairly small angular separation (e.g., ~15-20°) between the two x-ray sources is sufficient to give accurate 3D-2D registration and 3D localization of structures sufficient for surgical guidance (e.g., within ~2 mm). Such a small angular separation may not be sufficient for a human observer to "mentally" register/triangulate the position of structures within the 3D coordinate system, but it is sufficient for a robust registration algorithm as developed by the inventors.

In FIG. 2 two x-ray sources are implemented on a common platform (in this case, a mobile C-arm) with a single x-ray detector. The lined region exemplifies the approximate region of the x-ray beam associated with the primary source (which in FIG. 2 is depicted with the circle), and the dotted region exemplifies that of the auxiliary source (the auxiliary source is depicted in FIG. 2 with a dotted circle). An example application of the invention involves the primary source being used for radiographic/fluoroscopic visualization as usual, and used in combination with the auxiliary source for 3D-2D registration with a previously acquired CT (and structures defined therein) for overlay on the primary projection image. In addition, the primary source may operate at conventional x-ray techniques suitable to high-quality visualization, whereas the auxiliary source may operate at a potentially lower x-ray output suitable to purposes of registration.

FIGS. 3, 4, 5 and 6 show variations on the position of the auxiliary source in the exemplary embodiment of FIG. 2. Each example shows the auxiliary source (in the figures: the source with the dashed line) placed at 15° from the primary source (which is depicted with the circle in the figures), depicting the additional field of view provided by each configuration.

Figure 5:
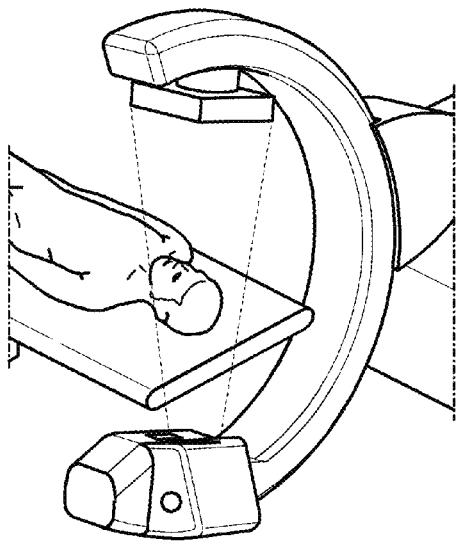
Figure 6:
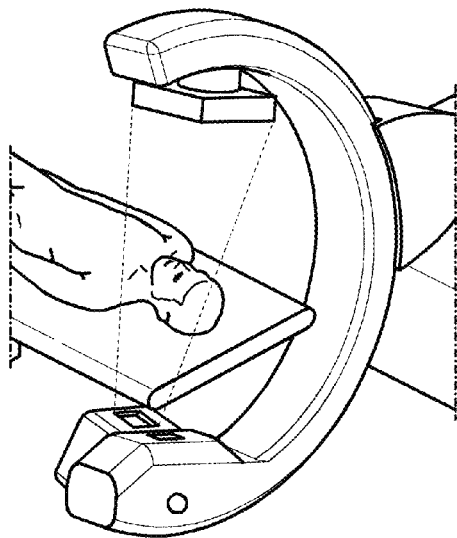

An auxiliary (potentially low-power) source attached to a mobile C-arm at a fixed (15-20°) or variable angular distance from the primary source, as depicted in FIG. 5.

Benefits of this system include accurate 3D localization and surgical guidance by way of improved 3D-2D registration via secondary view, repeatable (constant) angular difference between two views, eliminating the need for C-arm motion (hence also keeping the primary view focused at the desired region of interest).

The invention is anticipated to offer improved localization in 3D without the use of external tracking equipment (or in combination with such trackers), allowing a system to overlay, visualize, and/or quantitatively document:

preoperative or intraoperative 3D structures on the 2D radiograph;

intraoperative content (e.g. target location, position/orientation of surgical tools) within the 3D CT context via manual or automated extraction of features from 2D images.

An advantage of present application has to be seen in the improvement in 3D localization; i.e., solving for 6 degrees-of-freedom (DoFs), where the secondary radiograph improves the geometric accuracy of registration in 3 DoFs defined about the detector normal, as well as the minimum C-arm angulation required (<20°). Example radiographs of the spine could be provided by the reported invention (for use by the registration algorithm). The projection may be an example anterior-posterior (AP) view of for example a cadaver lying prone on the operating table. This is the type of view that might be used by the interventionalist to visualize anatomy and interventional devices—e.g., the small metallic probes (wires with markers at the tip) visible in four locations about the spine. The projection may be an image acquired at an angular separation of 20° from an AP view. The visual difference between the two images is subtle and not likely sufficient for a human observer to perform the type of "mental" registration/triangulation necessary for 3D localization. However, recent work by Uneri et al. shows that this level of angular separation is sufficient for the 3D-2D registration algorithm to compute an accurate 3D localization (i.e., <2 mm in the 3D domain of the patient). Additionally, it may be helpful to provide a further projection with an image acquired at an angle 90° from the AP view, representative of the type of "bi-plane" perspective offered by bi-plane fluoroscopy.

Figure 7:
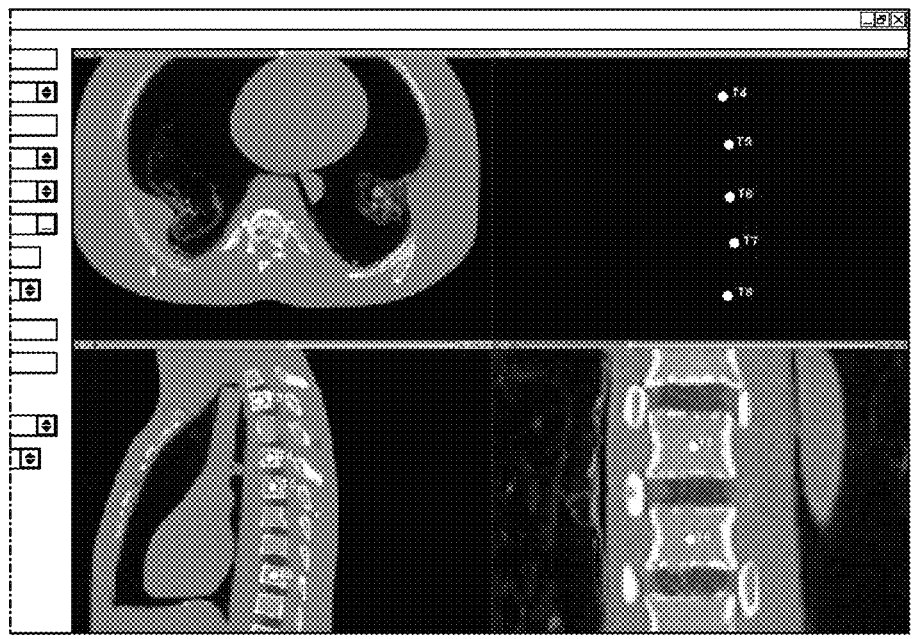
FIG. 7 is an exemplary representation of registered images of a chest phantom, provided by the 3D-2D registration process according to a preferred embodiment of present invention.

It has to be pointed out, that the present invention does not require the use of external trackers which is a major advantage of prior art registration procedures. 3D-2D guidance facilitated by the reported invention may be presented to the surgeon in a way that is currently achieved by external trackers, i.e. as 3D guidance within the preoperative context (FIG. 7). This is a potentially significant and disruptive technology in the context of image-guided surgery, since conventional tracking systems (e.g., infrared trackers, video-based trackers, electromagnetic trackers, etc.) have a variety of intrinsic limitations in accuracy as well as a variety of logistical burdens. The ability to provide surgical guidance from the C-arm itself could be a major change in streamlining and improving the precision of image-guided surgery.

A (medical) workflow involves acquisition of a 3D image within which structures of interest are identified. The preferred modality is CT, since it allows computation of digitally reconstructed radiographs (DRRs) in a manner compatible with the algorithm described in the current algorithm (Otake et al.). For example, the 3D image could be a CT acquired prior to the procedure.

Figure 8:
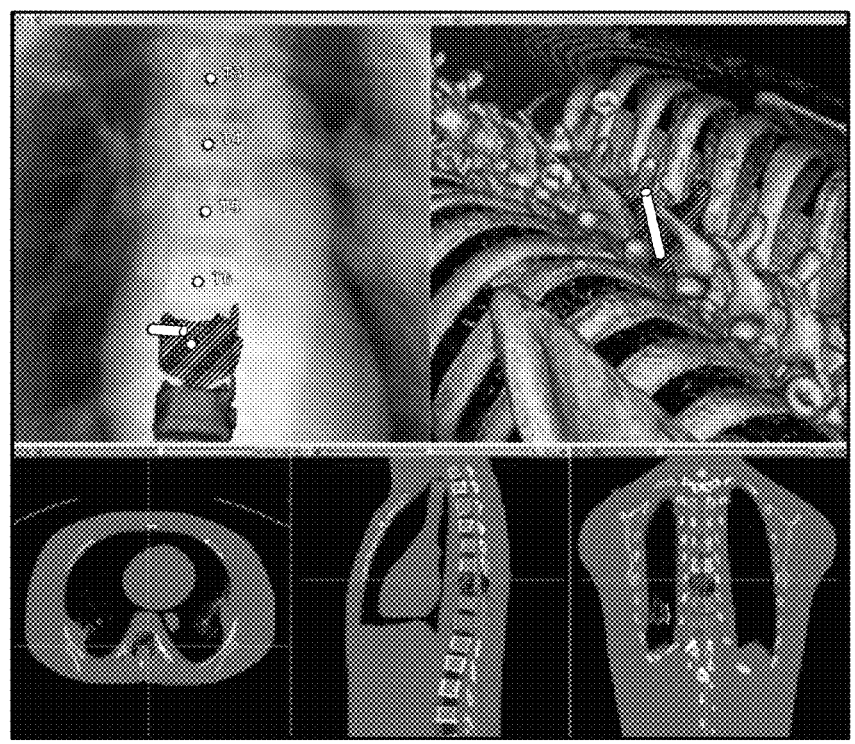
FIG. 8 is another exemplary representation of registered images of a chest phantom, provided by the 3D-2D registration process according to a preferred embodiment of present invention.

Structures defined in the 3D image include anatomy of interest, anatomical labels, contours, intended trajectories, device locations, etc. Examples are shown in FIGS. 7 and 8. Structure definition can be as simple as discrete anatomical points (e.g., a point marking the center of vertebrae as in FIG. 7) or as sophisticated as the trajectories, contours, and segmentations illustrated in FIG. 8.

FIG. 7 shows by way of example a 3D image providing input to the 3D-2D registration process—e.g., a CT image acquired prior to the procedure. FIG. 7 is a CT image of a chest phantom in which point structures marking the center of each vertebra have been defined (which in the images should be depicted with light grey points and/or reference numerals for the respective vertebra). FIG. 8 is a CT image of a chest phantom in which the trajectory of a needle (depicted as white structure in the left upper and right upper figure) along with segmentations of various vertebrae have also been defined. The panel in FIG. 8 also contains an example 3D-2D registered overlay of the point, trajectory, and contour overlays in an AP radiograph (which should be shown in FIG. 8 with marked regions hatched).

Referring to the step of acquiring at least two 2D images on an acquisition device, this may be done during intervention. 2D projection images are acquired using the proposed system. The primary source, for example, can be used to form fluoroscopic/radiographic images for visual interpretation, while the auxiliary source is used (possibly at reduced radiation output compared to the first source) for purposes of 3D-2D registration.

As an advantage, the invention allows for conventional fluoroscopy—e.g., using only the primary source—without 3D-2D registration (or with 3D-2D registration but with reduced depth resolution compared to the case in which two projections are acquired at disparate perspectives).

In the following the step of computing a 3D/2D registration is explained in more detail. Given the 3D image and the 2D image(s) described above, the 3D-2D registration is computed—e.g., using the algorithm reported by Otake et al. Other 3D-2D registration methods exist and are applicable to the proposed invention.

In the following the step of "outputting a result" is explained in more detail. The result may be used for localization and guidance of technical equipment during the surgical intervention. The process provides the information necessary for accurate overlay of 3D-2D registered information in projection images. Following the registration, structures defined in the 3D image can be accurately overlaid on the radiograph and—in addition, due to the accurate 3D localization provided by disparate perspective views—can provide 3D localization, such as the location of a device within the body relative to an anatomical structure of interest (e.g., guiding the surgeon in placing a needle in a tumor).

A variety of other embodiments of the invention can be envisioned and are described in more detail below.

Figure 9:
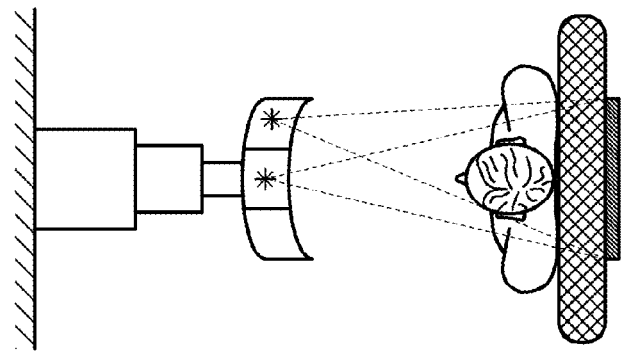
FIG. 9 shows a schematic drawing of a multi-source acquisition system according to an embodiment of present invention, in which with the sources are positioned on a room-mounted arm over an operating table.

FIG. 9 illustrates a configuration in which the multiple-source system is mounted on an adjustable boom (e.g., a ceiling-mounted arm) and the detector (which is depicted in the FIGS. 9 to 11 with a rectangle, hatched to the right) is positioned separately (e.g., under the operating table). The multiple-source unit above the table might provide a less obtrusive arrangement in comparison to a C-arm positioned at the side of the operating table. The detector could be any of various digital x-ray imaging devices (e.g., flat-panel detectors) that are common in digital radiography/fluoroscopy. For example, a wireless flat-panel detector with a compact form factor (e.g., Carestream DRX-1) could be easily integrated without major modification of the operating table. The separation of the source and detector provides potential logistical advantages (e.g., the absence of a C-arm device at table-side) but introduces additional degrees of freedom in the registration that must be solved. According to another embodiment of present invention the system is to include the ability to position the source unit at a desired source-detector distance as a reasonable initialization. It has to be noted that the problem has been solved in the context of mobile radiography, and the same solution could be applied here.

Figure 10:
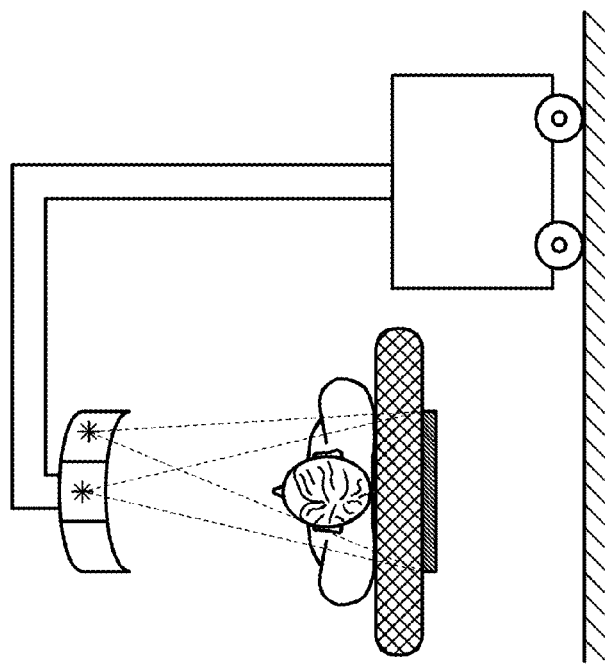
FIG. 10 is a schematic drawing of a multi-source acquisition system according to another embodiment of present invention, in which the sources are positioned on a mobile radiography cart over an operating table.

FIG. 10 illustrates a variation on the embodiment shown in FIG. 9 in which the multiple-source system is mounted on mobile radiography system (rather than a room-mounted arm). As in FIG. 9, the detector could be positioned under the operating table. The arrangement is potentially advantageous in cost (the mobile unit could service multiple operating rooms) and simplicity (mobile x-ray units are fairly common and may be more readily incorporated in existing operating rooms than a room-mounted system). The multiple-sources allow for accurate 3D localization for surgical guidance (which is not possible in prior art systems with only a single source).

Figure 11:
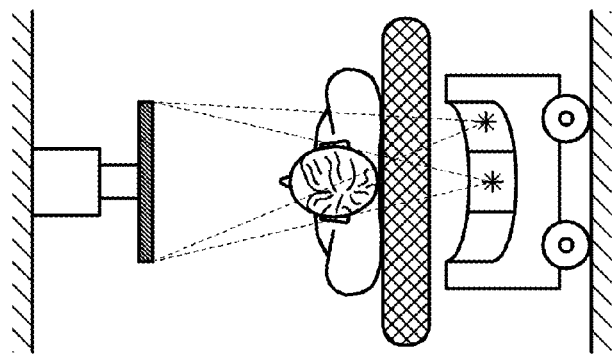
FIG. 11 is a schematic drawing of a multi-source acquisition system according to another embodiment of present invention, in which the sources are positioned on a mobile cart beneath an operating table.

FIG. 11 reverses the concepts shown in FIG. 9 and FIG. 10 such that the multiple-source system is positioned under the operating table (e.g., on a mobile x-ray unit), and the detector is positioned over the operating table (on a room-mounted adjustable arm or a mobile arm). The arrangement may be advantageous logistically (less obtrusive) and dosimetrically (exposure from beneath the operating table typically delivers less dose to the patient than exposure from over the table).

In the example alternative embodiments of the multiple-source/single-detector concept shown in FIGS. 9 to 11, in each case, the multiple-source system is marked by an enclosure with asterisks (* *), and the detector is marked by a dark black rectangle. In FIG. 9 a multiple-source system is suspended on an adjustable room-mounted arm over the operating table, with the detector positioned beneath the operating table. In FIG. 10 (as in FIG. 9) the multiple-source system is suspended on a mobile radiography cart. In the embodiment shown in FIG. 11, which is analogous to FIGS. 9 and 10 the multiple-source system is configured in a mobile cart positioned beneath the operating table, and the detector positioned over the table on an adjustable arm (or mobile cart).

Figure 12:
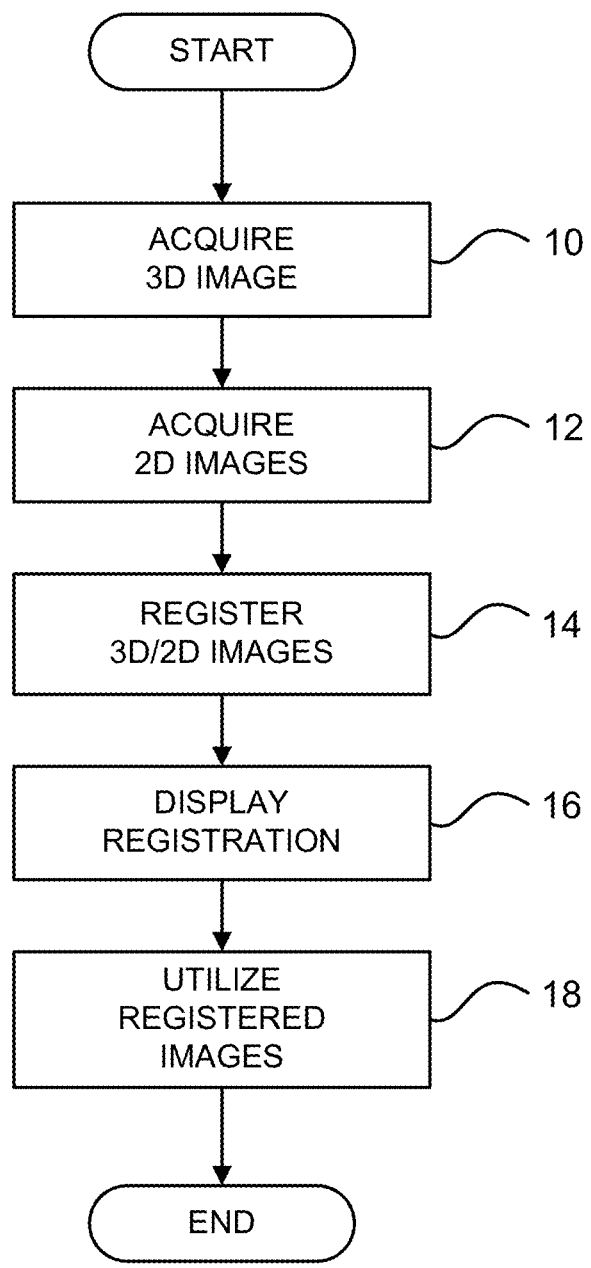
FIG. 12 is a flow chart of a typical workflow of a surgical guidance method according to a preferred embodiment of present invention.

FIG. 12 is a workflow showing a typical procedure according to an exemplary embodiment of the present invention. After start of the procedure, in step 10 at least one 3D image is acquired (for example by a normal CT Scanner) or provided from memory.

In step 12 at least two 2D images are acquired on the acquisition device in the specific configuration, having a primary source and at least one auxiliary source and one common detector for the primary and the auxiliary source.

In step 14 the 3D/2D registration of the provided 3D image and the acquired 2D images is computed in order to provide a result of the registration.

In step 16 this result of the computed registration is outputted in configurable manner. A graphical representation of the result may be visualized on a monitor.

Step 18 is optional and refers to surgical guidance and navigation based on the registered images (3D/2D images). After this the method ends. Alternatively, the result may be forwarded to other computer based instances for further processing.

The present invention, thus, refers to registration of e.g. preoperative CT to e.g. intraoperative fluoroscopy to provide a basis for 3D surgical guidance. The procedure is similar to that normally achieved via external tracking systems. There is a specific focus on registration using two fluoroscopic views acquired at angular separation ($\Delta\theta$) ranging from ~0° (single perspective) to ~90° (biplane fluoroscopy) and ~180° (opposing views). Furthermore experimental evidence is used to identify the minimum angular separation required to yield accuracy in 3D localization that is equivalent or better to that achieved with a conventional surgical tracking system (e.g., an EM tracking system capable of 3D localization within ~2 mm). Present invention enables accurate 3D surgical guidance without trackers—i.e., using the imaging system itself as a tracker (and the patient him/herself as the registration "fiducial") in a manner that potentially absolves the complexities associated with conventional navigational tools, such as manual setup using fiducials and/or fixation frames, line of sight (in optical tracking), metal artifacts (in EM tracking), additional equipment, and gradual deterioration of the image-to-world registration during the case.

In the following the 3D-2D registration algorithm will be described in more detail.

The algorithm for 3D-2D registration iteratively solves the transformation of a 3D image (e.g., preoperative or intraoperative CT) such that a 2D projection computed from the 3D image (i.e., a digitally reconstructed radiograph, DRR) yields maximum similarity to the intraoperative 2D image (e.g., x-ray radiograph acquired via C-arm fluoroscopy). This process amounts to calculation of the 6 degrees of freedom (DoF) of the patient pose that aligns the preoperative patient image and surgical plan with the actual 2D projection. The basic algorithm was described in detail in (Otake et al 2012) in application to labeling surgical targets (viz., vertebral levels—ergo, the "LevelCheck" algorithm), and a brief summary is provided below. We furthermore extend the registration process to multiple projection images such that a joint solution is simultaneously optimized for purpose of 3D localization (not just 2D overlay).

CT images are first converted from Hounsfield units (HU) to linear attenuation coefficients ($\mu$, units of $mm^{-1}$) based on the coefficient of water at an effective energy of the CT acquisition, and the intraoperative x-ray projections (radiography or fluoroscopy) are log-normalized. After this conversion, the similarity between the intraoperative radiograph ($p_1$) and a DRR ($p_2$) was defined in terms of the gradient information (GI) metric (Pluim et al 2000):

$$GI(p_1,p_2)=\Sigma_{(i,j)\in\Omega}w_{1,j}\min(|g_{1,j,1}|,|g_{1,j,2}|) \quad (1)$$

where i,j are pixel indices within the image domain $\Omega$, and the gradient (g) is $$g_{ij} = \nabla p(i, j) := \left(\frac{d}{di}p(i, j), \frac{d}{d,j}p(i, j)\right). \quad (2)$$

The weighting function (w) favors either small gradient angles (i.e., alignment of edges) or angles that are approximately equal to $\pi$ (i.e., opposing orientation):

$$w_{i,j} = \frac{1}{2}\left(\frac{g_{i,j,1}g_{i,j,2}}{|g_{i,j,1}||g_{i,j,2}|} + 1\right). \quad (3)$$

The use of GI was motivated in part by its robustness against potential mismatches between the images, since the min(*)operator ensures both images present strong gradients. Therefore, GI only accrues information that is common in both the radiograph and the DRR, and gradients present in only one of the images (e.g., a surgical device) do not contribute to GI. Similarly with respect to anatomical deformation, the similarity metric provides a degree of robustness by ignoring inconsistent gradients between deformed tissues and instead relies upon consistent information presented by locally rigid structures. The robustness against content mismatch is especially important in surgical guidance, considering the presence of surgical tools, variations in patient positioning, and deformations due to tissue manipulation.

When multiple (N) projections are provided, the respective similarity measures are summed up, such that $$g_{1,j}=\Sigma_{n=1}^{N}\nabla_{p_n}(i,j) \quad (4)$$

Handling multiple projections by a sum of gradients is equivalent to a composite approach in which multiple images are considered one large image, and a single similarity measure is computed. Other approaches, such as the alternating approach, use the similarity measure of only one image pair per iteration in the optimization in an alternating manner.

Figure 13:
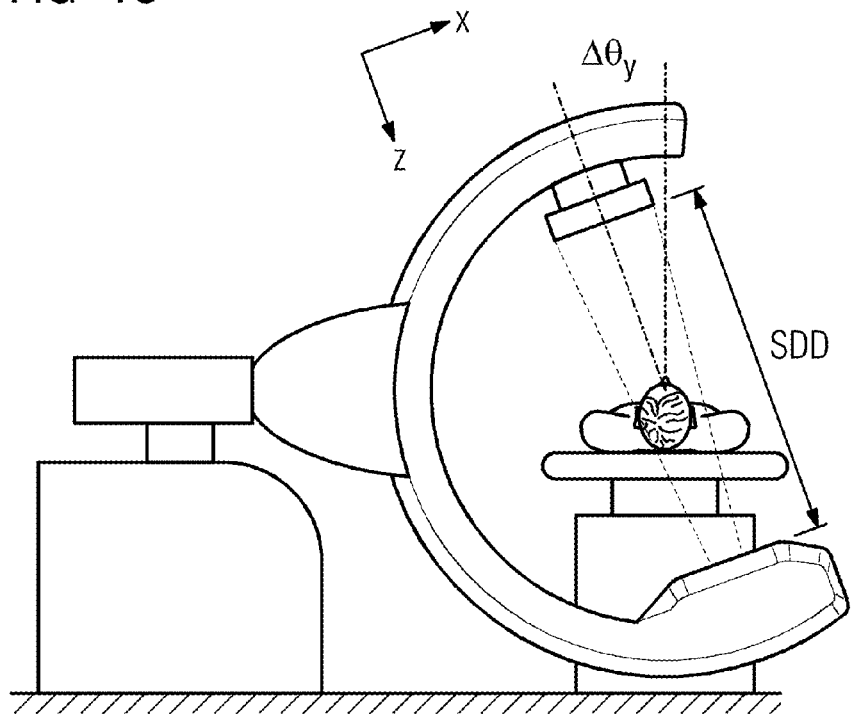
FIG. 13 and FIG. 14 are schematic illustrations of a C-arm geometry, the coordinate frame used, and possible angulations to achieve projection image pairs.

The optimization problem was therefore to solve for the six DoF transform maximizing GI:

$$\tau\frac{c\tau}{Fluoro} = \frac{\text{argmax}GI}{\tau}(p_1, p_2(\tau(t_x, t_y, t_z, r_x, r_y, r_z))) \quad (5)$$

where the 3D-2D registration $$\left(\tau \frac{CT}{Fluoro}\right)$$

was solved by an iterative search of the translation ($t_1x,t_1y,t_1z$) and rotation ($r_1x,r_1y,r_1z$) parameters, with (x,y,z) coordinates defined in FIG. 13. The covariance matrix adaptation evolution strategy (CMA-ES) (Hansen et al 2009) was employed, which generates a population ($\lambda$) of random sample points around the current estimate at each iteration, and evaluates the objective function (GI). The population is generated according to a multivariate normal distribution, where the mean and covariance of the distribution are updated per generation such that it is approximately aligned with the gradient direction of the objective. A major advantage of this stochastic approach is its robustness against local minima, in comparison to other derivative-based forms, though this same characteristic imparts a non-deterministic behavior; hence, the parameter values shown in Table 1 were selected to ensure repeatability.

TABLE 1

Summary of 3D-2D registration parameters and nominal values.

| Parameter | Symbol | Nominal Value |
|---|---|---|
| Initial registration | — | ~5-10 mm PDE |
| Optimizer population (offspring) size | $\lambda$ | 50 |
| Optimizer step size (standard deviation) | $\sigma$ | 5 {mm, °} |
| Optimizer [upper/lower] bounds | — | 10 {mm, °} |
| Optimizer stopping criterion (fitness) | — | 0.01 {mm, °} |
| Separation between projection views | $\Delta\theta$ | 0°-180° |
| C-arm geometric magnification | m | 2.0 |
| CT voxel size (slice thickness) | $a_z$ | 0.6 mm |
| Fluoro pixel size | $b_{u,v}$ | 0.6 mm |

The convergence of CMA-ES can be slow and require a large number of function evaluations, but the method is amenable to parallel evaluation as implemented on GPU and described below. It may also be implemented in a multi-resolution framework, which limits the local search space. Considering the application of interest in this study, in which projections are acquired in a consecutive manner throughout the procedure, each registration can initialize the next to within a local neighborhood of the solution. With the benefit of an initial global search that reduced the search space to within ~10 mm and ~10° (as described below), a multi-resolution scheme is not employed.

The algorithm was implemented utilizing the parallel computation capabilities of a graphics processing unit (GPU). The basic implementation was based on previous work (Otake et al 2012), where DRRs (digitally reconstructed radiographs) are generated via forward projection of 3D images using parallelized ray-tracing algorithms. A linear projection operator was used due to its low computational complexity and amenability to GPU (i.e., efficient use of hardware-accelerated interpolation, which is the texture fetching), using a step size equal to the voxel size. The Siddon projection algorithm (Siddon 1985) in which the analytically exact line integral was computed by accumulating the intersection length between the ray and intersecting voxels, was also implemented for use in experiments where the slice thickness was varied to remove potential biases due to arbitrary step-size selection. The GI similarity metric was also computed in parallel on GPU (c.f., non-local metrics such as mutual information, which require computing the joint histogram and are less amenable to parallel computation). Finally, the CMA-ES algorithm allowed computation of each sample of a generation in parallel.

A number of parameters governing the registration process are summarized in Table 1. Although the workflow envisioned (i.e., consecutive acquisition of fluoro shots without major changes in the anatomical scene) allows for strong initialization (i.e., the previous solution initializes the next), an initial global registration is still required at the beginning of the process. This global search was solved in previous work (Otake et al 2012), including conditions of strong deformation between the preoperative CT and intraoperative fluoroscopy, and its reported accuracy of ~5-10 mm projection distance error (PDE) was used as the basis for initialization in studies reported below. Initial registrations were thus obtained by randomly perturbing all 6 DoFs such that they produced at least 5 mm PDE. The optimizer step size and upper/lower bounds were selected accordingly, searching within ±10 {mm,°} for translation and rotation, respectively, with a standard deviation of 5 {mm,°}.

The optimization was terminated when the change at each coordinate was less than the stopping criterion. To ensure repeatable convergence, the stopping criteria and population size was tested over a range of 0.01-0.1 mm and 10-100, respectively. Both resulted in a reproducible transform (e.g., TRE with a standard deviation of $6\times10^{-2}$ mm), thus demonstrating convergence. The C-arm magnification and [axial] slice thickness of the input CT image were investigated as experimental parameters in studies described below. Binning of projection images to coarser voxel size was also considered, anticipating a dependency between the 2D pixel and 3D voxel sizes in obtaining a given level of registration accuracy.

Figure 14:
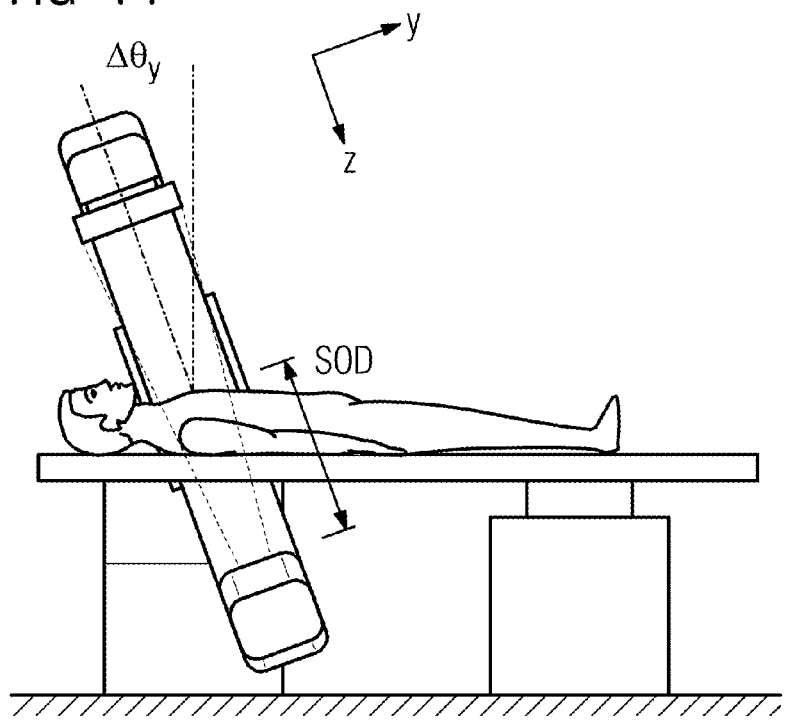

FIGS. 13 and 14 show a mobile C-arm geometry with possible angulations, $\Delta\theta$ about the longitudinal or lateral axis to achieve projection image pairs. Fluoroscopic images are acquired using a mobile C-arm incorporating a flat-panel detector and a motorized orbit. The C-arm geometry was calibrated using a spiral BB phantom and the resulting calibration was represented as projection matrices composed of intrinsic and extrinsic parameters describing the 3D position of the x-ray source with respect to the detector. The calibration parameters were also used to quantify the C-arm magnification $$m = \frac{SDD}{SOD},$$

where SDD and SOD denote the source-detector and source-object distance, respectively, as marked in FIGS. 13 and 14. Fluoroscopic images were acquired in a continuous orbit ($\Delta\theta_y$ direction in FIG. 13) spanning 178° yielding 200 projections at roughly equal increments of $\Delta\theta_y=0.9°$. Each projection image was $768^2$ pixels with 0.388 $mm^2$ isotropic pixel size. Projections acquired in this manner served two purposes:

a) any two projections (separated by different $\Delta\theta$) could be used to assess the angular dependence of the geometric accuracy; and b) each scan could be used to reconstruct a cone-beam CT (CBCT) image of the target anatomy.

The central result of the experiments used for this invention is the fairly small angular separation ($\Delta\theta \sim 10°$) in projection views required to achieve 3D localization accuracy (TRE<2 mm) comparable or superior to that of conventional surgical tracking systems (TRE may be construed as target registration error). The 3D-2D registration method yielded such accuracy across a very broad range in angular separation, with views at $\Delta\theta\sim15°$ providing equivalent accuracy to $\Delta\theta\sim90°$ (biplane). Interestingly, even 3D-2D registration from a single projection ($\Delta\theta=$) 0° performed approximately as well as the EM tracker (TRE~2.5-3 mm). The result invites analogy to depth perception in natural vision with a fairly small optical baseline, where in this case, the registration algorithm takes the place of biological neural processing of depth cues and stereovision.

While PDE is a prevalent metric for 3D-2D registration accuracy, TRE was shown to better characterize 3D localization, particularly in the range of small angular separation in which localization suffers from limited depth resolution. Cadaver experiments demonstrated that $\Delta\theta\sim10°$ angular separation was adequate to obtain TRE comparable or superior to that of commercial surgical trackers with 95% confidence. Nominal registration parameters were identified and drawn from previous work (Otake et al 2012), and other parameters that may vary across surgical procedures were investigated, including C-arm magnification, CT slice thickness, and detector pixel size.

The present application potentially extends the utility of x-ray fluoroscopy from that of qualitative depiction to one of quantitative guidance. By incorporation of the same prior information as in conventional navigation (viz., a 3D CT image and planning data), but without the need for trackers, fiducial markers, and stereotactic frames, accurate 3D localization is possible from projections acquired at a small) (~10° angular separation. The result suggests the potential of 3D guidance based on 3D-2D registration with or without conventional trackers. In such a scenario, the imager is the tracker, and the patient is the fiducial.

The workflow by which 3D-2D guidance might be achieved is somewhat different from that of conventional navigation. Specifically, the method does not operate in real-time (~30 sec registration time on the current GPU implementation), and it involves the delivery of radiation dose. With respect to the first point, one might argue that step-by-step presentation of guidance information with each fluoro shot is a good match to the surgeon's natural workflow, and the real-time (~30 fps) nature of conventional tracking systems is not essential in practice; "snapshot guidance" may suffice. With respect to the second point, the radiation dose in image-guided procedures must be minimized. The method described herein is intended to work within the context of fluoroscopically guided procedures, leveraging images that are already acquired for visualization of surgical progress to provide 3D guidance. In scenarios where a coarse level of localization accuracy is sufficient (e.g., TRE~3 mm, comparable to that of the EM tracker), the results suggest the capability to perform 3D guidance in a single projection ($\Delta\theta=0°$), implying no increase in radiation dose beyond that already employed for fluoroscopic visualization. In scenarios where a higher degree of accuracy is required (e.g., TRE~1.6 mm), a second projection view is required ($\Delta\theta\sim10°$ or more), implying a factor of 2 increase in total dose if the second view is acquired at dose equal to the first. Work underway investigates registration accuracy from data in which the second view is at significantly reduced dose, hypothesizing that the algorithm is sufficiently robust to quantum noise, and the increase in total dose would be incremental. Also, the guidance information provided in each fluoro shot may actually reduce the surgeon's need for repetitive fluoro shots (i.e., reduce total fluoro time), since s/he would rely less on qualitative image interpretation by virtue of quantitative localization. Finally, there is, of course, the scenario in which such 3D-2D guidance is deployed in concert with conventional tracking, integrating fluoroscopy with navigation in a manner that leverages each to maintain accuracy throughout the case and overcome the shortfalls of the other (e.g., line of sight, c.f., radiation dose).

Generally, the method according to the invention may be executed on an acquisition device and/or on one single computer or on several computers that are linked over a network. The computers may be general purpose computing devices in the form a conventional computer, including a processing unit, a system memory, and a system bus that couples various system components including system memory to the processing unit. The system bus may be any one of several types of bus structures including a memory bus or a memory controller, a peripheral bus and a local bus using any of a variety of bus architectures, possibly such which will be used in clinical/medical system environments. The system memory includes read-only memory (ROM) and random access memories (RAM). A basic input/output system (BIOS), containing the basic routines that have the functionality to transfer information between elements within the computer, such as during start-up, may be stored in one memory. Additionally, the computer may also include hard disc drives and other interfaces for user interaction. The drives and their associated computer-readable media provide non-volatile or volatile storage of computer executable instructions, data structures, program modules and related data items. A user interface may be a keyboard, a pointing device or other input devices (not shown in the figures), such as a microphone, a joystick, a mouse. Additionally, interfaces to other systems might be used, such as an interface to a radiological information system (RIS) or to a hospital information system (HIS). These and other input devices are often connected to the processing unit through a serial port interface coupled to system bus. Other interfaces include a universal serial bus (USB). Moreover, a monitor or another display device is also connected to the computers of the system via an interface, such as video adapter. In addition to the monitor, the computers typically include other peripheral output or input devices (not shown), such as speakers and printers or interfaces for data exchange. Local and remote computer are coupled to each other by logical and physical connections, which may include a server, a router, a network interface, a peer device or other common network nodes. The connections might be local area network connections (LAN) and wide area network connections (WAN) which could be used within intranet or internet. Additionally networking environment typically includes a modem, a wireless link or any other means for establishing communications over the network.

Moreover, the network typically comprises means for data retrieval, particularly for accessing data storage means like repositories and the like. Network data exchange may be coupled means of the use of proxies and other servers.

It has to be pointed out that the method changes and transforms physical subject matter as images are generated and stored differently, namely with a specific 3D/2D registration procedure. Further, the physical architecture of the acquisition device has been changed compared to normal C-arms or x-ray based devices.

REFERENCES

Hansen N, Niederberger A S P, Guzzella L and Koumoutsakos P 2009 A Method for Handling Uncertainty in Evolutionary Optimization With an Application to Feedback Control of Combustion IEEE Transactions on Evolutionary Computation 13 180-97.
Otake Y, Schafer S, Stayman J W, Zbijewski W, Kleinszig G, Graumann G, Khanna A J, and Siewerdsen J H. "Automatic localization of vertebral levels in x-ray fluoroscopy using 3D-2D registration: a tool to reduce wrong-site surgery", Phys Med Biol 57(17):5485-508 (2012).
Pluim J P, Maintz J B and Viergever M a 2000 Image registration by maximization of combined mutual information and gradient information. IEEE transactions on medical imaging 19 809-14.
Siddon R L 1985 Fast calculation of the exact radiological path for a three-dimensional CT array. Med Phys 12 252-5.
Vahala E, Ylihautala M, Tuominen J, Schiffbauer H, Katisko J, Yrjänä S, Vaara T, Ehnholm G and Koivukangas J 2001 Registration in interventional procedures with optical navigator. Journal of magnetic resonance imaging: JMRI 13 93-8.
Weese J, Penney G P, Desmedt P, Buzug T M, Hill D L G and Hawkes D J 1997 Voxel-based 2-D/3-D registration of fluoroscopy images and CT scans for image-guided surgery IEEE Transactions on Information Technology in Biomedicine 1 284-93.

The invention claimed is:

1. A method for automatically registering medical images, the method comprising the following steps:
providing a 3D image;
acquiring at least two 2D images on an acquisition device having a primary x-ray source and at least one auxiliary x-ray source and one common detector for the primary and auxiliary x-ray sources, and having an angular separation of about 15-20 degrees between the primary and auxiliary x-ray sources;
computing a 3D/2D registration of the 3D image and the acquired 2D images; and
outputting a result of the computed 3D/2D registration.

2. The method according to claim 1, wherein the acquisition device is a 3D image acquisition device selected from the group consisting of: CT, SPECT, MR, linear accelerator with on-board x-ray imaging, C-arm with 3D imaging capability, and an x-ray-based modality.

3. The method according to claim 1, wherein the step of outputting the result comprises visualizing a common representation of the registered 3D and 2D images.

4. The method according to claim 1, wherein the step of outputting the result comprises controlling a medical intervention by providing 3D surgical guidance and navigation means.

5. The method according to claim 1, wherein the 2D images are not acquired concurrently to an acquisition of the 3D image.

6. The method according to claim 5, which comprises acquiring the 2D images during a medical intervention.

7. The method according to claim 1, which comprises acquiring the 2D images in parallel with an acquisition of the 3D image.

8. The method according to claim 1, wherein the step of computing the 3D/2D registration comprises:
iteratively computing a 2D projection view from the 3D image;
computing a target 2D projection view that best matches the acquired at least two 2D images by using a numerical optimization that maximizes similarity between the target 2D projection view and the acquired at least two 2D images.

9. The method according to claim 7, wherein an update frequency for computing the 3D/2D registration is not equal to an update frequency of acquiring the at least two 2D images.

10. An image acquisition apparatus for medical imaging, comprising:
a primary x-ray source;
at least one auxiliary x-ray source;
a detector for receiving radiation of said primary and auxiliary x-ray sources;
an interface to a registration unit, wherein the registration unit is configured to compute a 3D/2D registration of a provided 3D image and at least two acquired 2D images according to the method of claim 1; and
an output interface configured to provide an output for displaying the registered images on a monitor.

11. The image acquisition apparatus according to claim 10, wherein the image acquisition apparatus is adapted to provide the 3D image and the at least two 2D images.

12. The image acquisition apparatus according to claim 10, wherein the 3D image is acquired by a CT-scanner.

13. The image acquisition apparatus according to claim 10, wherein said primary and at least one auxiliary x-ray sources are mounted on a common support structure, and said common support structure is at least one of a ceiling-mounted support member or is mounted on a moveable arm.

14. The image acquisition apparatus according to claim 10, wherein said primary and at least one auxiliary x-ray source are mounted on a common support structure positioned beneath an operating table and said detector is mounted above the operating table.

15. A non-transitory computer readable medium containing computer-readable instructions stored therein for causing a computer processor to perform the steps of the method according to claim 1.

* * * * *